US008956425B2

(12) United States Patent
Irving

(10) Patent No.: US 8,956,425 B2
(45) Date of Patent: Feb. 17, 2015

(54) BIOFUELS CONTAINING NITRILE MOIETIES

(75) Inventor: Nicholas M. Irving, Guatemala (GT)

(73) Assignee: Rio Oeste, S.A., Guatemala (GT)

( * ) Notice: Subject to any disclaimer, the term of this patent is extended or adjusted under 35 U.S.C. 154(b) by 665 days.

(21) Appl. No.: 11/776,056

(22) Filed: Jul. 11, 2007

(65) Prior Publication Data
US 2008/0289247 A1   Nov. 27, 2008

(30) Foreign Application Priority Data

May 25, 2007 (GT) .............................. A-200700043

(51) Int. Cl.
| C10L 1/23 | (2006.01) |
| C10L 1/00 | (2006.01) |
| C07C 253/22 | (2006.01) |
| C07C 255/03 | (2006.01) |
| C07C 255/07 | (2006.01) |
| C10L 1/14 | (2006.01) |
| C10L 1/228 | (2006.01) |
| C11C 3/00 | (2006.01) |
| C10L 1/188 | (2006.01) |
| C10L 1/19 | (2006.01) |
| C10L 1/224 | (2006.01) |

(52) U.S. Cl.
CPC ............... *C10L 1/00* (2013.01); *C07C 253/22* (2013.01); *C07C 255/03* (2013.01); *C07C 255/07* (2013.01); *C10L 1/14* (2013.01); *C10L 1/2286* (2013.01); *C11C 3/00* (2013.01); *C10L 1/1881* (2013.01); *C10L 1/19* (2013.01); *C10L 1/224* (2013.01); *C10L 2200/0469* (2013.01); *C10L 2200/0476* (2013.01); *C10L 2230/22* (2013.01); *Y02E 50/13* (2013.01)
USPC ............................................................ 44/307

(58) Field of Classification Search
USPC ............................................................ 44/307
See application file for complete search history.

(56) References Cited

U.S. PATENT DOCUMENTS

| 2,061,314 A | 11/1936 | Ralston | |
| 2,135,327 A * | 11/1938 | Conquest | 44/384 |
| 2,444,828 A * | 7/1948 | Kaplan | 558/309 |
| 2,808,426 A * | 10/1957 | Potts et al. | 558/313 |
| 4,164,506 A | 8/1979 | Kawahara et al. | |
| 4,234,509 A | 11/1980 | Billenstein et al. | |
| 4,695,411 A | 9/1987 | Stern et al. | |
| 4,801,730 A | 1/1989 | Stuehler et al. | |
| 5,703,264 A | 12/1997 | Yoshida et al. | |
| 5,743,923 A | 4/1998 | Davies et al. | |
| 5,965,764 A * | 10/1999 | Matsuoka et al. | 558/311 |
| 6,005,134 A * | 12/1999 | Terasaka et al. | 558/311 |
| 6,391,996 B1 | 5/2002 | Scherer et al. | |
| 6,403,745 B1 | 6/2002 | Scherer et al. | |
| 6,592,639 B2 | 7/2003 | Bernasconi et al. | |
| 2005/0283011 A1 | 12/2005 | Hoong et al. | |
| 2007/0007176 A1 | 1/2007 | Pinho et al. | |
| 2008/0229654 A1* | 9/2008 | Bradin | 44/308 |

FOREIGN PATENT DOCUMENTS

| EP | 665873 B1 | 7/1996 |
| GB | 981123 A | 1/1965 |

OTHER PUBLICATIONS

Dorado et al, "Testing Waste Olive Oil Methyl Ester as a Fuel in a Diesel Engine." Energy and Fuels, vol. 17, No. 6, p. 1560-1565, 2003.
Dorado et al., "Optimization of Alkali-Catalyzed Transesterification of *Brassica carinata* Oil for Biodiesel Production" Energy and Fuels, vol. 18, No. 1, p. 77-83, 2004.
Ooi et al. "Catalytic Cracking of Used Palm Oil and Palm Oil Fatty Acids Mixture for the Production of Liquid Fuel: Kinetic Modeling" Energy and Fuels, vol. 18, No. 5, p. 1555-1561, 2004.
Wildes. "Clean Machines for Beams." Chemical Innovation, May 2001, p. 23-27.
McCoy, "An Unlikely Impact Growth of Biodiesel has big Implications for the Oleochemical." C&EN news, Feb. 21, 2005, p. 19.
Vogel "A Text-Book of Practical Organic Chemistry including Qualitative Organic Analysis." , prep. III, 111, Longmans, Green and Co., London, 1978.
March, "Advanced Organic Chemistry" 3rd Edition, Wiley-Interscience, New York, 1985 pp. 429-430, 742, 806-807, 856, 863, 930-934, 1061-1062, 1107-1109.
CRC Handbook of Chemistry and Physics, 56th Ed., Table D-274, 1975.

(Continued)

*Primary Examiner* — Prem C Singh
*Assistant Examiner* — Ming Cheung Po
(74) *Attorney, Agent, or Firm* — Brown & Michaels, PC

(57) ABSTRACT

A novel method to prepare high-enthalpy biofuels has been developed based on a new chemical pattern which has never been used before in the synthesis of renewable fuels. These biofuels are based on natural oleaginous feedstock, rendering low viscosity liquids with broad liquid range and enthalpy levels much superior to those found in common biodiesel, meaning ethyl or methyl fatty esters. As in the case of biodiesel, these new biofuels contain zero sulfur, causing none of the major pollution associated with commercial diesel. High enthalpy biofuels are aliphatic nitrile compounds, containing a single nitrogen substituent, are chemically aprotic, even though their high degree of polarity is reflected in its high cetane index and solubility parameter. The present invention includes fuels associated with diesel, as well as other high-enthalpy fractions, which according to their boiling point, correspond to naphtha in the lower scale, and bunker in the upper scale.

38 Claims, No Drawings

(56) References Cited

OTHER PUBLICATIONS

International Search Report and Written Opinion of the International Searching Authority for PCT/US2008/064659, dated Sep. 30, 2008.

Extended European Search Report for EPO application No. 08756178.3, Issued on Jan. 2, 2013, 8 pages.

* cited by examiner

BIOFUELS CONTAINING NITRILE MOIETIES

REFERENCE TO RELATED APPLICATIONS

This application claims one or more inventions which were disclosed in Guatemalan patent application number A-200700043, filed May 25, 2007, entitled "Biocompuestos de Function Nitrilo". The benefit under 35 U.S.C. §119(a) of that application is hereby claimed, and the aforementioned application is hereby incorporated herein by reference.

BACKGROUND OF THE INVENTION

1. Field of the Invention

The invention pertains to the field of biofuel production. More particularly, the invention pertains to biofuel compositions containing nitrile moieties and methods for production thereof.

2. Description of Related Art

Recently, as petroleum stocks dwindle, much emphasis has been given to the development of biofuels. In particular, alcohol is blended with naphtha to make gasohol, or is chemically bound to fatty acids to produce biodiesel. Conventional biodiesel is a fatty acid ester of lower alcohols, methanol in particular (and ethanol to a lesser extent), the former, known as fatty acid methyl ester is abbreviated FAME. One advantage of FAME relative to commercial diesel (from petroleum) is its negligible sulfur content, the presence of which contributes to acid rain formation. An additional advantage of FAME is its excellent lubricity, which is superior to that of commercial diesel fuel. Ironically, the little lubricity found in the commercial diesel fuel is directly linked to the presence of sulfur contaminants, and thus as levels of sulfur diminish, so does the internal lubricity of the fuel. In some parts of the world 0.3% sulfur is still acceptable, although that is still highly polluting. Biofuels compositions of the present invention also have essentially no sulfur content and thus their combustion does not contribute to acid rain.

Black exhaust smoke is another known problem of commercial petroleum diesel fuels, and is directly related to the nature of the hydrocarbons found in the fuel. Hydrocarbon fractions have both aromatic and aliphatic components, and the former contribute significantly to the formation of black smoke and soot. Aromatic hydrocarbons are found in all commercial diesels, yet are totally absent in biofuels like FAME. Not only do aromatics produce more smoke, but they also reduce the quality of diesel fuel by lowering the cetane index. Biofuels produce a lesser amount of smoke.

Cetane Index is a measure the speed of combustion by auto-ignition under pressure and is of importance in the quality of diesel fuel. The higher the Cetane index, the faster the combustion, and the higher the mechanical work output. Indices of 40 and 45 are the present minimums acceptable in the US and Europe, respectively. Most biofuels, however, are closer to the 60 mark, including FAME and the novel nitrile biofuels covered in the present invention. Cetane index in commercial diesel fuels can vary substantially, depending on their sources, which are quite diverse. In general, higher percentages of aliphatic hydrocarbons gives a higher cetane index, and the reverse is true for higher percentages of aromatic hydrocarbons.

Viscosity and liquid range are two additional factors that affect the quality of diesel fuels. Preferably, fuel intended for diesel motors has a viscosity under about 10 centistokes (ctsk), and a liquid range broad enough to prevent freezing of fuel lines in the winter. Diesel injectors work against tremendous internal cylinder pressure, and proper fluidity in fuel lines is therefore important. This is one reason why natural oils cannot be employed directly, and are instead modified through chemical reactions to provide derivatives with proper viscosity and liquid ranges.

First Generation Biodiesel

Renewable fuel of the FAME type is the generic biodiesel known to most people, and is commonly made by a transesterification reaction involving triglycerides and lower alcohols like methanol and ethanol. The method appeared in the patent literature about two decades ago, specifically in U.S. Pat. Nos. 4,164,506 and 4,695,411, as well as in a number of chemical publications, for example Dorado, Ballesteros et al, *Energy and Fuels,* 17(6), 1560 (2003). To this date there is ongoing research in the area of fatty acid esterification for fuel applications. In transesterification reactions, triglycerides of olive, soybean, sunflower, and palm oils react with lower alcohols in alkaline medium (S. Bhatia et al, Energy and Fuels, 18(5), 1555 (2004)). Transesterification is a relatively complex process (M. P. Dorado et al., Energy and Fuels, 18(1), 77 (2004)) in which several side reactions can affect yields in an adverse way. The fundamental reaction involves replacement of a glycerin group by lower alcohols, (S. G. Wildes, Chemical Innovation, May 2001, p. 23). The net reaction is shown below as the transesterification of a fatty (R) triglyceride with methanol:

Equation 1

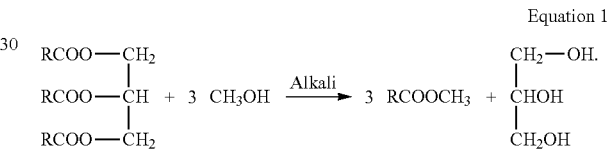

The reaction product is the fatty acid methyl ester $RCOOOCH_3$, or FAME, along with glycerin formed as a by-product. FAME type biodiesels are regarded as the first generation of such renewable fuels, commonly known as "biodiesel".

Acceptance of biodiesel is still a gradual process. Supply is constrained by the chemistry in transesterification, which is largely a batch operation. This fuel is being used in public transportation, some trucks, and farm equipment, and is usually blended with petroleum diesel. The US armed forces use large amounts of biodiesel, as a 20% blend in petroleum diesel, called B20 (M. McCoy, C&ENews, Feb. 21, 2005, p 19).

Second Generation Biodiesel

At this time there is a second generation of biodiesel under development. The process involves the pyrolysis of triglycerides, which can be conducted jointly with crude oil refining. The Resulting fatty carboxylic acids can be esterified directly, yielding esters akin to FAME through acid-catalyzed direct esterification (N. Irving, Guatemalan Patent Application A2006,0473) as shown in Equation 2 below:

Equation 2

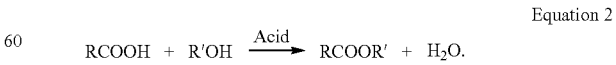

Methanol is the preferred alcohol for steric reasons. The resulting products are considered hybrid fuels.

In a more recent work (US Pat. Application 2007/0007176 A1) researchers used catalytic pyrolysis to promote decarboxylation of fatty acids resulting from pyrolysis of triglycerides. Pyrolysis is conducted at temperatures between 350 and 400° C., and $CO_2$ is described as a by product. A difference between these two processes is that in the first case acrolein is generated during triglyceride pyrolysis. In the process of the '176 application work neither glycerin nor acrolein are mentioned as being by products.

Despite the advantages described above, FAME type fuels are deficient in energy content in comparison to petroleum diesel fuels. The ester functional group of FAME contains a highly oxygenated carbon atom. This functional group contributes appreciable weight to the molecules, but it does not contribute significantly to the energy output of the fuel during combustion since the ester carbon is already in the oxidation state of $CO_2$. Thus there exists a need for a biofuel that retains the advantages of FAME, but which has a high energy content similar to petroleum derived fuels.

The present invention also pertains to methods for producing fatty aliphatic nitrile compositions from oleaginous feedstocks. Methods are known in the art for the production of aliphatic nitrites, however, none of the known methods are suitable for the large scale production of fatty aliphatic nitrites. One known route to nitrile compounds is by conversion of amides. The amide function —$CONH_2$ can undergo dehydration leading to the formation of a nitrile moiety along with loss of one water molecule. It is possible to conduct amide dehydration under atmospheric pressure, although only with great difficulty, requiring special conditions like flash pyrolysis or exceptionally strong dehydrating agents. A classic example is the formation of acetonitrile by dehydration of acetamide using phosphorous pentoxide as the dehydrating agent (Equation 2B) in a constant distillation process under atmospheric pressure as the reagents are heated (A. Vogel, *Practical Organic Chemistry*, prep. III, 111, Longmans, Green and Co., London).

Equation 2B

This method would not be industrially viable in the present case due to the cost of phosphorous pentoxide, which is employed in relatively large quantities. It would be very expensive to prepare fuels and solvents in bulk quantities by this method.

Compounds with carboxylic functionalities can be derivatized with the nitrile function by other known methods, none of which is viable in an industrial scale (see J. March, *Advanced Organic Chemistry*, $3^{rd}$ Edition, Wiley-Interscience, New York, 1985).

For example: Nitriles have been formed by treating carboxylic acids with trifluoroacetic acid anhydride and sodium nitrite. Alkali carboxylic acid salts have been treated directly with cyanogen bromide BrCN, and the intermediate formed decarboxylated to form the corresponding nitrite. Carboxylic acid esters, have been treated with an aluminum dialkyl amide (e.g. $(CH_3)_2AlNH_2$), to yield nitrites directly. Finally, a carboxylic acid chloride can react with ammonia forming the amide which can then be dehydrated as described above. Even though each of these methods allows conversion of a carboxyl derivative into a nitrile moiety, none of them is suitable for efficient industrial nitrile production from fatty acids. The present invention provides methods which can effectively convert fatty acid feedstocks into aliphatic nitrile compositions on a substantial scale.

SUMMARY OF THE INVENTION

The present invention discloses liquid compositions of aliphatic nitrile compounds derived from fatty acid feedstocks similar to those used to produce FAME biofuels. One embodiment of the invention is directed to nitrile-containing biofuels which are high energy biodiesel (HEBD) fuels having an energy content higher than FAME and close to that of commercial petroleum-based diesel. HEBD retains the advantages of the known renewable fuels, namely: negligible sulfur content, superior cetane index, low viscosity, good liquid range, and excellent internal motor lubricity.

Other embodiments of the invention provide aliphatic nitrile compositions suitable for other uses including, but not limited to, jet fuel, kerosene replacements, gasoline or gasoline additives or supplements, high boiling compositions for replacing petroleum bunker, and compositions suitable for use as plasticizers and solvents.

The present invention also discloses methods for producing liquid aliphatic nitrile compositions from lipid feedstocks such as vegetable oils or animal fats or oils, or other natural oleaginous sources. If desired, other industrial intermediates such as purified fatty acids, esters or amides can be used as feedstocks. In a preferred embodiment, the fatty aliphatic nitrile compositions can be made by a unique continuous method.

DETAILED DESCRIPTION OF THE INVENTION

The present invention provides new compositions of aliphatic nitrile compounds and methods suitable for their industrial production from oleaginous natural sources having carboxyl functional groups (—COO—). In one embodiment of the invention, a natural oleaginous raw material, either vegetable or animal, is derivatized to arrive at an aliphatic bio-compound bearing a nitrile functionality R—CN.

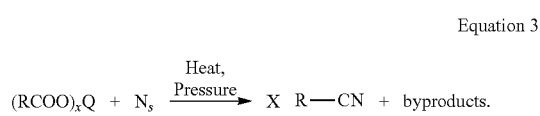

Equation 3

In equation 3, Q is a moiety belonging to the initial oleaginous material, for example, a hydrogen atom in the case of fatty acids, a carbon fragment from an alcohol or polyol in the case of fatty acid esters or glycerides, a phosphate moiety in the case of phospholipids, or a carbohydrate moiety in the case of glycolipids. The variable X in equation 3 is typically the integer one or three. $N_s$ is a chemical reagent that acts as a nitrogen source. Representative examples of nitrogen sources that can be employed in the process of equation 3 include: ammonia, urea, biuret, ammonium carbonate, ammonium bicarbonate, and ammonium carbamate. The product R—CN is an aliphatic nitrile or a mixture of aliphatic nitrites having R groups corresponding to the aliphatic sidechains present in diverse oleaginous sources of natural origin, or in some instances, aliphatic fragments of those sidechains. The presence of nitrile groups in products of equation 3 has been confirmed by FTIR spectroscopy on samples herein prepared.

The present invention also provides compositions of fatty aliphatic nitrile compounds thus produced. These compositions are suitable for diverse uses including: as a fuel for internal combustion engines; as plasticizers; and as polar aprotic solvents.

An attractive use for compositions of the present invention is as biofuels, and particularly as biodiesel compositions. As mentioned above, viscosity, liquid range, cetane index, sulfur content, and lubricity are all important parameters for diesel fuel. Compositions of the present invention have values of all of these parameters which make them suitable for biofuel applications.

Viscosity is understood as resistance to flow, a property which depends on temperature, chemical structure and molecular volume, molecular weight, hydrogen bonding, and secondary forces. Liquid range depends on the same factors as viscosity, although to a different degree, in addition to the degree of purity of the substance involved. That is the reason for employing, for example, soybean methyl ester (5 to 6 cstk) as opposed to pure soybean oil (60 to 90 cstk) in diesel engines. Heat values of both are comparable, and even lubricity is comparable. However, soybean oil is too viscous for most diesel motor injectors. A paraffinic hydrocarbon having boiling range of 240 to 320° C. is ideal as a diesel fuel and has a fairly low viscosity. If this hydrocarbon is compared with a typical triglyceride (such as the one in Equation 1), a structural difference stands out, the branched structure in the latter makes flow difficult due to entanglements. Following Equation 1, when FAME is formed, four molecular changes occur simultaneously. First, the branched structure disappears. Second, molecular weight is reduced. Third, molecular polarity increases significantly. Fourth, a hydrogen-bonding acceptor system arises for potential hydrogen bonding donors.

If, instead of forming FAME, the corresponding carboxylic acid RCOOH is formed, the first three molecular changes mentioned before would take place, and the fourth factor would become more complicated due to the presence of a full donor-acceptor hydrogen bonding system. As a consequence, the carboxylic acid group cannot flow and solidifies readily (i.e. melting point increases). If as an alternative, the corresponding fatty alcohol $RCH_2OH$ is formed, a reasonably good diesel fuel would result, having somewhat higher viscosity due to the donor-acceptor hydrogen bonding character. A similar case would occur with the homologous fatty amine $RCH_2NH_2$, which would also have a good liquid range, would have even lesser viscosity than the previous alcohol, and would have even higher enthalpy of combustion. However, it would not be useful due to its high corrosiveness. If, in its place the fatty amide RCONH2 is prepared, the problem of corrosiveness is ameliorated, but the low viscosity would be lost again, along with the liquid range since this highly polar compound undergoes extensive hydrogen bonding.

In view of the requirements for a good diesel fuel, the nitrile group —CN is an attractive option since it fulfills all of the requirements listed herein, and since it has a high enthalpy of combustion. Furthermore, the nitrile group is high in symmetry as a consequence of its sp hybridization which, being linear, presents less resistance to flow, meaning lower viscosity. Nitrile is also a functional group with a high degree of chemical stability, being aprotic, reasonably inert and having a very good solubility parameter.

As discussed above, the extent of oxygenation of nitrile compounds is less than that of ester compounds. In the case of FAME biodiesel, there are two oxygen atoms per molecule, a fact that results in a serious enthalpy deficit. The effect of the degree of oxidation on enthalpy value is demonstrated by comparing the molar heat of combustion (CRC, 56$^{th}$ Ed., D-274) divided by the molecular weight for representative compounds. The correlation is appreciated by comparing a series of compounds with same number of carbon atoms, for example the $C_4$ compounds in Table I given below:

TABLE I

Heats of Combustion (Kcal/g) of Series $C_4$

| Compound | $H_c°$, Kcal/g |
|---|---|
| $C_4H_{10}$ | 11.90 |
| $C_3H_7COOH$ | 5.93 |
| $C_3H_7CN$ | 8.88 |
| $C_2H_5$—OOCCH$_3$ | 6.10 |

The enthalpy of combustion per gram of compound decreases with an increase in the extent of oxidation. Butane, a paraffin with four carbons, has the maximum comparative heat value and is the reference for the corresponding C-4 family.

The same trend was shown using experimental data in the present invention. (ASTM D-240, Ministry of Energy and Mines, Guatemala, Order L-212-07) Heat of combustion of commercial diesel fuel was used as reference, and this value compared to that of palm oil-derived FAME as well as HEBD originating from the same palm oil. The data are presented in Table II as listed below:

TABLE II

Heats of Combustion (Kcal/g) of Diesel, FAME, and HEBD

| Sample | $H_c°$, Kcal/g | % Ref. Diesel |
|---|---|---|
| Diesel | 10.65 | 100 |
| FAME | 9.39 | 88 |
| HEBD | 10.33 | 97 |

The similarity of HEBD's heat of combustion to that of commercial diesel stands out, being 97%. In contrast, FAME, a traditional biodiesel, shows only 88% of the enthalpic value of commercial diesel fuel. This increased energy content in HEBD is a significant improvement over existing FAME biofuels.

Other applications of the liquid nitrile containing compositions of the present invention include their use as non-protic polar solvents, and as plasticizers. The properties of the compositions can be controlled to suit a particular application by judicious choice of feedstocks, or by fractionating the crude products to afford compositions with specific boiling ranges, or polarity profiles.

TABLE III

Nitrile Bio-Fuel Classification by Boiling Ranges

| Fuel Fractions | Boiling Range, ° C. |
|---|---|
| Naphtha | <190 |
| Kerosene | 190 to 240 |
| Diesel | 240 to 320 |
| Bunker | >320 |

For instance, with the methods of the present invention one can produce aliphatic nitrile compositions suitable to replace traditional petroleum refinery fractions such as naphtha, kerosene, diesel, and bunker (see Table III). Nitrile compositions with boiling ranges similar to these petroleum products can be isolated from the processes described below.

The chemistry employed to produce nitrile compositions of the present invention is summarized in Equation 3 above. This equation can be expanded into more specific embodiments, which differ depending on the oleaginous material being used and the source of nitrogen employed ($N_s$). In each case, the end products have the same generic structure R—CN and are primarily aliphatic nitriles with sidechains substantially corresponding to the fatty acid sidechains present in the starting materials. It is to be understood that a given chemical process may encompass several intermediate steps and may produce various synthetic intermediates which may vary depending on the reagents that are employed. The following reactions are exemplary embodiments of the present invention where, for simplicity, reaction intermediates that may be formed such as carboxylic salts and amides are not explicitly shown.

In one embodiment of the present invention shown in Equation 4, a fatty acid is reacted with urea to yield fatty aliphatic nitriles, carbon dioxide and water:

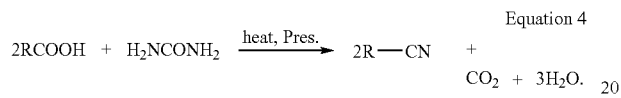

Equation 4

In another embodiment of the present invention shown in Equation 5, a fatty acid is reacted with ammonia to afford the fatty nitriles and water:

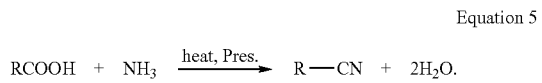

Equation 5

In the embodiment of the present invention shown in Equation 6, a triglyceride is reacted with urea to provide fatty aliphatic nitriles, carbon dioxide, water, and glycerol and/or glycerol decomposition products:

(RCOO)₃Q+1.5H₂NCONH₂→3R—CN+1.5CO2+ 4.5H2O+(glycerol or its fragments)  Equation 6.

In the embodiment of the present invention shown in Equation 7, a triglyceride reacts with ammonia to provide fatty aliphatic nitriles, water, and glycerol (a similar reaction occurs with ammonium carbonate, ammonium carbamate, or ammonium bicarbonate as the nitrogen source).

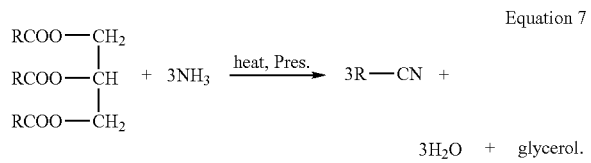

Equation 7

The processes of the present invention summarized in Equation 3 are preferably conducted under rigorously controlled conditions with respect to heat (H), pressure (P), and temperature (T), as well as with careful control of chemical equilibrium through mass transfer. If the reaction is conducted under unsuitable conditions, the desired product is not obtained since the reaction becomes stuck in intermediate products instead of the end product. For example, if a fatty carboxylic acid and ammonia are mixed under ambient conditions, the ammonium salt of the carboxylic acid is obtained according to Equation 8:

Equation 8.

Such a salt is relatively unstable, and can decompose back into its initial components. However, if the same salt is heated under pressure, it can undergo controlled dehydration forming the corresponding amide.

Equation 9

Amides can also be obtained directly from triglycerides, as shown below. One known method is the treatment of an ester, in this case the triglyceride directly with ammonia, which frees glycerol as the alcohol and forms the amide.

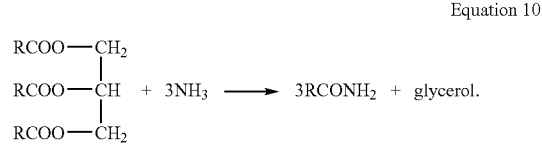

Equation 10

In the present study, it was shown that it is possible to react the same triglyceride directly with urea, wherein a catalytic presence of water promotes the initial decomposition of urea, allowing ammonia liberated in situ to react according to Equation 10.

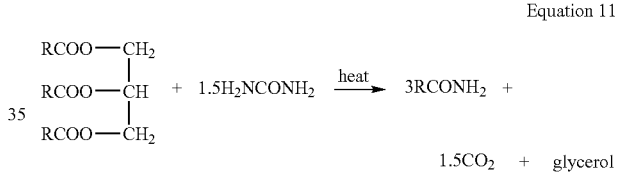

Equation 11

Finally, those intermediates involved in Equations 4 and 5 are also amides having the general formula RCONH₂. It may be desirable to arrive at the intermediate amide of general formula RCONH₂ in a first step, followed by its dehydration in a separate step to afford the final nitrile product. In the present invention, fatty amides were dehydrated under high temperature conditions and under pressure, releasing water gradually as it was formed upon decomposition of the amide group. If pressure is not applied, the primary result is distillation of the amide without appreciable dehydration. Additionally, if the pressure is not released gradually as water is being formed, the process is not brought to conditions of equilibrium irreversibility. This way, while the amide is subject to temperatures between 200 to 400° C. under pressures up to about 400 psi, preferably under 200 psi, by allowing gradual reduction of pressure from water of dehydration, fatty aliphatic nitriles of corresponding fatty amides are obtained in high yields.

One embodiment of this process entails relieving the pressure gradually as water is formed by the dehydration reaction. By maintaining a selected head pressure, the amide is not allowed to boil, or worse, to froth beyond control. In a preferred embodiment of the invention, the pressure during this stage is advantageously maintained between about 20 to about 60 psi. Reaction irreversibility is achieved either through the partial liberation of pressure, which allows water vapor to leave the system, or by the introduction of a cold condensation trap internally in the system, with the trap temperature low enough to freeze water as it vaporizes and reaches the trap. This trap should preferably be insulated from the reactor, which is hot. By introducing irreversibility in the system aliphatic nitrile products are formed.

EXAMPLES

Example 1

In a 350 mL pressure vessel 100 g of palm oil were introduced, followed by 10.9 g of urea. The mixture was heated under stirring in a water bath in order to become as homogeneous as possible, the vessel was sealed tightly, and heated to 270° C. The internal pressure reached 180 psi and was released in a controlled way. The intermediate product had a melting point of 75° C., and heating proceeded with periodic depressurizations. At 360° C. and 100 psi, an aqueous condensate was obtained. The temperature reached 380° C. and 100 psi, while gradual depressurization continued until no significant pressure build up was observed. The yield was 85 g of a liquid product.

Example 2

In a 350 mL pressure vessel 100 g of palm oil were introduced, followed by 13 g of urea and 4 mL of water. After mixing well and closing the vessel tightly, the mixture was heated gradually while gas build up was depressurized frequently. Water soluble condensate was obtained beyond 360° C., and heating continued up to 380° C. with consecutive depressurization, until there was no significant pressure build up. Eighty grams of liquid product were obtained.

Example 3

In a 1 L beaker 185 g of raw palm oil were introduced, followed by 24.1 g of urea and 3 mL of water. After mixing well, the beaker was heated in the open up to 200° C. until gas evolution stopped while keeping foam under control. The product was transferred to a 350 mL pressure vessel, and sealed tightly. There were 4 g of solid product left in the beaker, which were later determined to contain phosphorous. The reactor was heated with frequent depressurization up to 372° C., at which point there was no more significant pressure build up. 150 g of liquid were obtained, which was distilled under atmospheric pressure and the fraction boiling between 220 and 320° C. was collected. Product density was 0.811 g/mL and viscosity 6.07 cstk.

Example 4

In a 500 mL Erlenmeyer flask, 100 g of purified lauric acid and 30 g of urea were introduced, mixed well, and then heated to 165° C., holding this temperature until gas evolution subsided. Next, the temperature was brought up to 225° C., and an intermediate product with a fairly high melting point was obtained. This intermediate was transferred to a 350 mL pressure vessel, sealed tightly, and heated to 380° C. with frequent depressurizations. This product was distilled under atmospheric pressure, and the fraction boiling between 190 to 280° C. was collected. A thin liquid of 4.46 cstk and density 0.809 g/mL was obtained.

Example 5

A mixture of 137 g of purified soybean oil and 17.2 g of urea was prepared, and stirred well. Then it was transferred into a 350 mL pressure vessel, sealed tightly, and gradually heated to 380° C. with frequent depressurizations. The yield was 120 g of liquid plus 17 g of aqueous condensate in the exit tube. The liquid was distilled and the fraction between 180 to 320° C. was collected. This liquid had a viscosity of 11.1 cstk and density 0.840 g/mL.

Example 6

In a 650 mL beaker 100 g of palm oil were mixed well with 30 mL of aqueous ammonia, covered tightly, and allowed to stand for 1 day at ambient temperature. Next the mixture was heated in a water bath, which caused some froth and spillover. After excess ammonia was evaporated, the product was transferred to a 350 mL pressure vessel, and heated gradually up to 380° C. with the system connected internally to a trap kept in dry ice. The liquid was distilled at atmospheric pressure, to afford a product having a viscosity of 5.8 cstk, and density 0.827 g/mL.

Example 7

In a stainless steel pressure vessel 500 g of soybean oil and 500 g of palm oil were pyrolyzed and the carboxylic acid distillate mixed under vigorous mechanical agitation while 500 mL of concentrated aqueous ammonia was added at 25° C. After heating to 75° C. for 2 h, the product was freed of excess ammonia, heated for 1 h at 140° C., and vented carefully until pressure leveled off. Then the mixture was heated under increasing pressure, releasing vapors gradually between 300 and 390° C. until no significant further pressure build up occurred. The product was distilled at atmospheric pressure, and the fraction boiling between 240 and 300° C. was collected.

Example 8

A 5 mL sample of the product from Example 5 was applied to an alkyd enamel finish on a metal surface, causing the coating to wrinkle and blister in a few minutes.

Example 9

A 5 mL sample form the product of Example 4 was applied to small pieces of polystyrene, causing this plastic to soften and dissolve partially in a few minutes.

Example 10

The process described in Example 7 was repeated on a scale corresponding to 2 Kg of each oil, and the product blended with equal parts of commercial diesel fuel. This fuel blend was tested in a diesel engine, and worked perfectly.

Example 11

A mixture of 400 g of carboxylic acid from palm oil and 400 g of carboxylic acid from soybean oil was heated with 140 g of urea in a 2 L stainless vessel under mechanical agitation for 2 h at 180° C., and then transferred to a 4 L pressure vessel. This same procedure was repeated, while the amide mixture in the pressure vessel was heated to 350° C., depressurized to 40 psi as soon as 100 psi were reached, and then the product removed by simple distillation when pressure remained below 20 psi. Both procedures were repeated in a semi-continuous, encompassed sequence. In a cycle, 590 g of liquid boiling between 160 to 320° C. (7.8 cstk, 0.828 g/mL) were obtained, plus 145 g of un-distilled, hydrocarbon-soluble, heavy liquid.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for preparation of a liquid aliphatic nitrile containing composition comprising the steps of:
   a) mixing a source of fatty acid sidechains with a nitrogen source to form a mixture;
   b) heating the mixture at an elevated pressure in a sealable vessel;
   c) while heating, removing water generated by reaction from the mixture with control of heat, pressure, temperature, and chemical equilibrium through mass transfer to drive a reaction of the source of fatty acid sidechains with the nitrogen source irreversibly to form liquid aliphatic nitriles; and
   d) distilling a liquid product containing nitrile derivatives of the fatty acid sidechains formed from the reaction mixture and collecting a first distillate of the liquid aliphatic nitrile containing composition for use as a biodiesel fuel.

2. The method of claim 1 wherein the method comprises a continuous feed operation and wherein the starting materials are replenished and recovery of the liquid product containing nitrile derivatives is performed by continuous separation of nitrile products from the reaction mixture.

3. The method of claim 1 further comprising, between step (c) and step (d), a step selected from the group consisting of: cooling the mixture, relieving the elevated pressure, and cooling the mixture and relieving the elevated pressure.

4. The method of claim 1, wherein the nitrogen source is selected from the group consisting of:
   a) urea;
   b) biuret;
   c) ammonium carbonate;
   d) ammonium bicarbonate;
   e) ammonium carbamate; and
   f) any combination of (a) through (e).

5. The method of claim 1, wherein the source of fatty acid sidechains is selected from the group consisting of:
   a) a fatty acid;
   b) a fatty ester;
   c) a fatty amide;
   d) a polyglyceride;
   e) a phospholipid;
   f) a glycolipid;
   g) an animal-derived oil or fat;
   h) a plant-derived oil or fat; and
   i) any combination of (a) through (h).

6. The method of claim 1 further comprising, between step (a) and step (b), a step of heating the mixture at atmospheric pressure.

7. The method of claim 1 wherein the mixture is heated to between about 150° C. and about 450° C. in step (b).

8. The method of claim 1 wherein step (b) further comprises the substeps of:
   i) heating and holding the mixture at a first temperature of between about 100° C. and 200° C., and
   ii) heating the mixture to a second temperature of between about 200° C. and about 450° C.

9. The method of claim 8 wherein:
   during substep i) the pressure in the sealable vessel is maintained at from about 20 psi to about 40 psi; and
   during substep ii) the pressure in the sealable vessel is maintained at a pressure from about 20 psi up to about 400 psi.

10. The method of claim 1 wherein water is removed from the mixture by releasing vapor from the sealable vessel as the water is formed.

11. The method of claim 1 wherein water is removed from the reaction by condensing the evolved water vapor with a cold trap.

12. The method of claim 1, wherein the pressure is maintained at between about 20 psi and about 400 psi in steps (b) through (c).

13. The method of claim 1, wherein the pressure is maintained at between about 20 psi and about 100 psi in steps (b) through (c).

14. The method of claim 1, wherein step (d) comprises the substep of distilling the reaction mixture.

15. The method of claim 1 further comprising the step of sealing the sealable vessel.

16. The method of claim 1, wherein the step of removing water from the mixture comprises a plurality of controlled, periodic, gradual, partial depressurizations of the sealable vessel, while maintaining a head pressure selected to retain generated amides.

17. The method of claim 1, wherein the step of removing water from the mixture exclusively drives the reaction of the source of fatty acid sidechains with the nitrogen source irreversibly to form liquid aliphatic nitriles.

18. The method of claim 1, wherein:
   step (b) comprises the substep of heating the sealable vessel to a reaction temperature such that at the elevated pressure, water is formed by the reaction, thereby increasing the pressure in the reaction vessel; and
   step (c) comprises the substep of periodically gradually releasing excess pressure from water formation in the sealable vessel in a plurality of controlled, partial depressurizations of the sealable vessel, while maintaining a head pressure selected to retain generated amides, until no further pressure buildup is observed when the sealable vessel is sealed, thereby driving the reaction of the source of fatty acid sidechains with the nitrogen source irreversibly to form liquid aliphatic nitriles.

19. The method of claim 16, wherein the head pressure is at least 40% of the elevated pressure.

20. The method of claim 19, wherein the head pressure is 56% of the elevated pressure.

21. The method of claim 1 consisting essentially of steps (a), (b), (c), and (d).

22. The method of claim 1, wherein the source of fatty acid side chains comprises at least one polyglyceride.

23. The method of claim 22, wherein the nitrogen source comprises urea.

24. The method of claim 22, wherein the at least one polyglyceride comprises at least one triglyceride.

25. The method of claim 1, wherein the first distillate is collected at a boiling temperature above about 240° C. and below about 320° C. at atmospheric pressure.

26. The method of claim 25, wherein step (d) further comprises the sub-step of collecting a second distillate boiling below 190° C. at atmospheric pressure for use as a naphtha fuel.

27. The method of claim 26, wherein the second distillate is a higher enthalpy biofuel than fatty acid methyl ester (FAME) biodiesel with a heat of combustion of about 110% relative to fatty acid methyl ester (FAME) biodiesel.

28. The method of claim 25, wherein step (d) further comprises the sub-step of collecting a third distillate boiling above 190° C. and below 240° C. at atmospheric pressure for use as a kerosene fuel.

29. The method of claim 25, wherein step (d) further comprises the sub-step of collecting a residue remaining at 320° C. at atmospheric pressure for use as a bunker fuel.

30. The method of claim 1, wherein the first distillate is collected at a boiling temperature above about 220° C. and below about 320° C. at atmospheric pressure.

31. The method of claim 1, wherein the first distillate is collected at a boiling temperature above about 190° C. and below about 280° C. at atmospheric pressure.

32. The method of claim 1, wherein the first distillate is collected at a boiling temperature above about 160° C. and below about 320° C. at atmospheric pressure.

33. The method of claim 1, wherein the first distillate is collected at a boiling temperature above about 180° C. and below about 320° C. at atmospheric pressure.

34. The method of claim 1, wherein the first distillate has a heat of combustion of about 10.33 Kcal/g.

35. The method of claim 1, wherein the first distillate has a heat of combustion of about 97% relative to petroleum diesel.

36. The method of claim 1, wherein the first distillate is a higher enthalpy biofuel than fatty acid methyl ester (FAME) biodiesel with a heat of combustion of about 110% relative to fatty acid methyl ester (FAME) biodiesel.

37. The method of claim 1, wherein the first distillate is usable as a fuel in a diesel engine.

38. The method of claim 1, wherein the mixture initially further comprises a catalytic presence of water to promote a decomposition in situ to produce ammonia.

* * * * *